United States Patent [19]

Hack et al.

[11] 4,004,913
[45] Jan. 25, 1977

[54] SELECTIVE HERBICIDAL COMPOSITIONS

[75] Inventors: Helmuth Hack, Odenthal-Hahnenberg; Ferdinand Münz, Schildgen; Ludwig Eue, Cologne; Werner Schäfer, Leverkusen, all of Germany

[73] Assignee: Bayer Aktiengesellschaft, Leverkusen, Germany

[22] Filed: May 26, 1972

[21] Appl. No.: 257,366

[30] Foreign Application Priority Data

June 12, 1971 Germany .......................... 2129199

[52] U.S. Cl. ........................................ 71/90; 71/92
[51] Int. Cl.² ........................................ A01N 9/12
[58] Field of Search ........................................ 71/90

[56] References Cited
FOREIGN PATENTS OR APPLICATIONS 7,009,136  12/1970  Netherlands .......................... 71/90

*Primary Examiner*—Glennon H. Hollrah
*Attorney, Agent, or Firm*—Burgess, Dinklage & Sprung

[57] ABSTRACT

Selective herbicidal compositions comprising as active ingredients:

a. imidazolidin-2-one-1-carboxylic acid isobutylamide of the formula

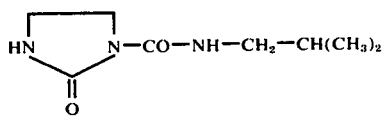

and b. 1-methyl-3-(2-benzothiazolyl)-urea of the formula

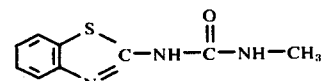

or 3-cyclohexyl-5,6-trimethylene-uracil of the formula

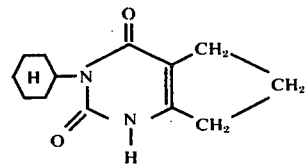

are particularly useful in selective destruction of weeds in beet cultivation.

2 Claims, No Drawings

SELECTIVE HERBICIDAL COMPOSITIONS

The present invention relates to new synergistic combinations of a certain imidazolidine compound and a certain urea compound or uracil compound, which compounds are, per se, old.

The synergistic combinations display a particularly high selective herbicidal action when combating weeds in beet cultivation. The imidazolidine compound is the known material imidazolidin-2-one-1-carboxylic acid isobutylamide.

With respect to the urea or uracil compound, it has already been disclosed that 1-methyl-3-(2-benzothiazolyl)-urea can be used as a herbicide, for example in beets; see U.S. Pat. No. 2,756,135 and Belgian Pat. No. 647,740. Furthermore it has already been disclosed that 3-cyclohexyl-5,6-trimethylene-uracil can be used as a herbicide in U.S. Pat. No. 3,235,360. It has also been disclosed that imidazolidin-2-one-1-carboxylic acid isobutylamide can be used as a herbicide, in Belgian Pat. No. 737,449. The uracil, the urea and the imidazolidinone compounds have the disadvantage, as selective herbicides in beets, that with the large number of weeds which occur in beets they do not destroy all of them adequately. The weeds which cannot be combated then spread unusually rapidly, since they grow without competition from the other weeds, and cancel the initial success of a treatment with the herbicide.

Belgian Pat. No. 752,516 further discloses that combinations of active compounds containing imidazolidin-2-one-1-carboxylic acid isopropylamide, 1-methyl-3-(2-benzothiazolyl)-urea and/or 3 cyclohexyl-5,6-trimethylene-uracil can be used as beet herbicides.

The present invention provides a selective herbicidal composition for use in beet cultivation, containing as active ingredients:

a. imidazolidin-2-one-1-carboxylic acid isobutylamide of the formula

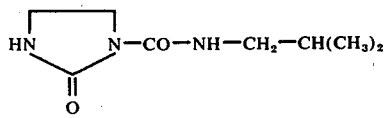

(I)

and b. 1-methyl-3-(2-benzothiazolyl)-urea of the formula

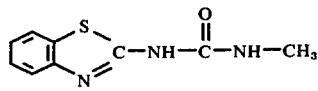

(II)

or 3-cyclohexyl-5,6-trimethylene-uracil of the formula

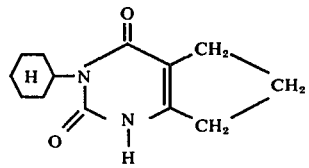

(III)

alone or in admixture with a solid or liquid or liquefied gaseous diluent or carrier.

The invention also provides a method of combating weeds in beet cultivation which comprises applying to the cultivation a composition as defined in the last paragraph above.

The invention also provides beet crops protected from damage by weeds by being grown in aread in which, immediately before or during the time of growing, such a composition was applied.

Surprisingly, the effectiveness of the active compound combinations according to the invention is substantially greater than the sum of the effects of the individual active compounds. An unforeseeable genuine synergistic effect exists, and not merely an additive effect. This synergistic effect manifests itself particularly strongly at certain concentration ratios, as indicated below.

The active compound combinations according to the invention are superior to previously known active compounds for combating weeds in beets; in particular they show a particularly broad and, according to a greenhouse test, a particularly good selective herbicidal action in beets as compared to the active compound combinations which are known (from Belgian Pat. No. 752,516) and contain imidazolidin-2-one-1-carboxylic acid isopropylamide, 1-methyl-3-(2-benzothiazolyl)-urea and/or 3-cyclohexyl-5,6-trimethylene-uracil. Hence the active compound combinations represent a valuable enrichment of the art of beet cultivation.

Imidazolidin-2-one-1-carboxylic acid isobutylamide, 1-methyl-3-(2-benzothiazolyl)-urea and 3-cyclohexyl-5,6-trimethylene-uracil are known. If the active compound combination comprises imidazolidin-2-one-1-carboxylic acid isobutylamide and 1-methyl-3-(2-benzothiazolyl)-urea, the weight ratio of the two active compounds relative to each other is generally from 0.25 : 1 to 4 : 1, preferably 0.5 : 1 to 2 : 1.

If the active compound combination comprises imidazolidin-2-one-1-carboxylic acid isobutylamide and 3-cyclohexyl-5,6-trimethylene-uracil, the weight ratio of the two active compounds relative to each other is generally from 1.5 : 1 to 9 : 1, preferably 3 : 1 to 5 : 1.

In normal use, the active compound combinations according to the invention show a very good action against weeds without harming the beets.

By weeds in the present sense there are to be understood the undesirable plants which usually occur in beet cultivations, for example fodder beet cultivations and sugar beet cultivations.

As examples of weeds which are destroyed by the combinations of the invention and which frequently occur in beets, there may be mentioned: dicotyledons, such as common persicaria (*Polygonum persicaria*), deadnettle (*Lamium spec.*), common chickweed (*Stellaria media*), fat hen (*Chenopodium album*), gallant soldier (*Galinsoga spec.*), fumitory (*Fumaria officinalis*) and ivy-leaved speedwell (*Veronica hederifolia*); and monocotyledons, such as annual bluegrass (*Poa annua*) and black grass (*Alopecurus myosuroides*).

The active compound combinations according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, e.g., aerosol propellants, such as halogenated hydrocarbons, e.g., freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates; and preferred examples of dispersing agents include lignin, sulphite waste liquors and methyl cellulose.

The combinations of active compounds according to the invention may be present in the formulations in admixture with other active compounds, such as other herbicides and fungicides.

The formulations contain, in general, from 0.1 to 95, preferably 0.5 to 90, percent by weight of total active compounds.

The active compound combinations can be used in the form of their formulations or of the use forms prepared therefrom, such as ready-to-use solutions, emulsions, suspensions, powders, pastes and granules. They may be applied in the usual manner, for example by atomizing, spraying, watering, dusting or scattering.

The active compound combinations can be used after the emergence of the plants but are preferably used before emergence of the plants.

The amounts used of the active compound combinations can be varied within a certain range. They depend on the composition of the active compound combinations and on the particular weeds in the beet cultivation. In general, the amounts used are from 1 to 6, preferably 3 to 5 kg of total active ingredients per hectare of cultivation.

The good herbicidal action of the active compound combinations is shown by the Example which follows. Whilst the individual active compounds show shortcomings in the herbicidal action, the combinations show a very broad effect on weeds, which exceeds a simple sum of the effects.

A synergistic effect exists in selective herbicides if the herbicidal effect of the active compound combination on the weeds is as great or greater than the herbicidal effect of the more active individual active compound on the weeds and at the same time the herbicidal effectiveness of the active compound combination on the crop plant is less than the herbicidal effectiveness on the crop plant of the particular individual component which is best tolerated by the crop plant. In these cases the selectivity and hence the pesticidal value are thus unmistakably increased. What is to be expected with active compound combinations without a synergistic effect is merely a broadening of the spectrum of action, but not an increase in the selectivity.

The table of the Example clearly shows that the active compound combination according to the invention displays a genuine synergistic effect. The herbicidal effect of the active compound combination is always at least as great as the herbicidal effect of the more active individual active compound, whilst at the same time the beets are less damaged or endangered.

EXAMPLE

Pre-emergence test

Solvent: 5 parts by weight of acetone
Emulsifier: 1 part by weight of alkylaryl-polyglycol-ether.

To produce a suitable preparation of active compound, 1 part by weight of active compound is mixed with the stated amount of solvent, the stated amount of emulsifier is added and the concentrate is then diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the test plants is determined and characterized by the values 0–5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The active compounds, the amounts applied and the results obtained can be seen from the following Table.

Table

| | | Pre-emergence test | | | | | |
|---|---|---|---|---|---|---|---|
| Active compound | Amount used in kg/ha | Beets | Stellaria media | Fumaria officinalis | Galinsoga spec. | Chenopodium album | Poa annua |
| (1) 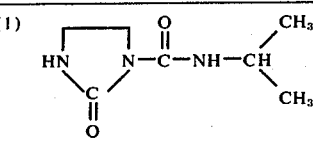 | 6 | 1.5 | 3.5 | 4.5 | 5 | 5 | 5 |
| | 4 | 0 | 2.5 | 3 | 4 | 4 | 4 |

Table-continued

| | | Pre-emergence test | | | | | | |
|---|---|---|---|---|---|---|---|---|
| | Active compound | Amount used in kg/ha | Beets | Stellaria media | Fumaria officinalis | Galinsoga spec. | Chenopodium album | Poa annua |
| (2) | (known) [benzothiazolyl urea structure] | 6<br>4 | 0.5<br>0 | 5<br>4 | 3.5<br>3 | 5<br>4 | 4.5<br>3.5 | 5<br>4 |
| | (known) Mixtures of (1) and (2), weight ratio 2 : 1 (known). | 6<br>4 | 1.5<br>0 | 5<br>4 | 4.5<br>3 | 5<br>4 | 5<br>4 | 5<br>4 |
| (3) | [imidazolidinone structure] (known) | 6<br>4 | 0<br>0 | 3.5<br>2.5 | 4.5<br>3.5 | 5<br>4 | 4.5<br>4 | 5<br>4 |
| | Mixture of (2) and (3), weight ratio 2 : 1 (according to the invention) | 6<br>4 | 0<br>0 | 5<br>4 | 5<br>3.5 | 5<br>4.5 | 5<br>4 | 5<br>4 |
| | Mixture of (2) and (3), weight ratio 0.5 : 1 (according to the invention) | 6<br>4 | 0<br>0 | 4.5<br>4 | 5<br>4 | 5<br>4.5 | 5<br>4 | 5<br>4 |
| (4) | [cyclohexyl amide structure] (known) | 1.5<br>1 | 2<br>1 | 5<br>4.5 | 5<br>4 | 5<br>5 | 5<br>4 | 5<br>4.5 |
| | Mixture of (1) and (4), weight ratio 3 : 1 (known). | 5<br>3 | 1.5<br>0 | 5<br>4 | 5<br>3.5 | 5<br>4.5 | 5<br>4 | 5<br>4 |
| | Mixture of (3) and (4), weight ratio 3 : 1 (according to the invention) | 5<br>3 | 0<br>0 | 5<br>4.5 | 5<br>4 | 5<br>5 | 5<br>4 | 5<br>4.5 |
| | Mixture of (3) and (4), weight ratio 5 : 1 (according to the invention) | 5<br>3 | 0<br>0 | 5<br>4.5 | 5<br>4.5 | 5<br>5 | 5<br>4 | 5<br>4.5 |

What is claimed is:

1. Selective herbicidal composition comprising, as active ingredients, in effective amounts
   a. imidazolidin-2-one-1-carboxylic acid isobutylamide of the formula

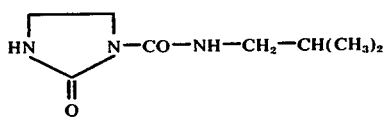

and
   b. 1-methyl-3-(2-benzothiazolyl)-urea of the formula

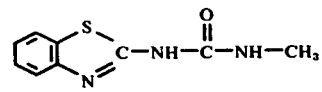

wherein the weight ratio of (a) to (b) is 0.5:1 to 5:1.

2. Herbicidal composition as claimed in claim 1 in which the said ratio is 3:1 to 5:1.

* * * * *